(12) United States Patent
Majeti et al.

(10) Patent No.: US 10,780,175 B2
(45) Date of Patent: Sep. 22, 2020

(54) POLYMER SYSTEMS AND THEIR APPLICATIONS IN DIAGNOSTICS AND DRUG DELIVERY

(71) Applicant: The Texas A&M University System, College Station, TX (US)

(72) Inventors: Naga Venkata Ravi Kumar Majeti, College Station, TX (US); Prabhjot Saini, Greenville, TX (US); Raghu Ganugula, College Station, TX (US); Meenakshi Arora, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/567,370

(22) PCT Filed: Apr. 18, 2016

(86) PCT No.: PCT/US2016/028104
§ 371 (c)(1),
(2) Date: Oct. 17, 2017

(87) PCT Pub. No.: WO2016/172042
PCT Pub. Date: Oct. 27, 2016

(65) Prior Publication Data
US 2018/0110865 A1    Apr. 26, 2018

Related U.S. Application Data

(60) Provisional application No. 62/149,563, filed on Apr. 18, 2015.

(51) Int. Cl.
| | | |
|---|---|---|
| *C08G 63/91* | (2006.01) |
| *A61K 31/198* | (2006.01) |
| *A61K 31/337* | (2006.01) |
| *A61K 31/352* | (2006.01) |
| *A61K 31/585* | (2006.01) |
| *A61K 47/60* | (2017.01) |
| *C08G 63/664* | (2006.01) |
| *C08G 63/685* | (2006.01) |
| *A61K 47/59* | (2017.01) |
| *A61K 47/69* | (2017.01) |
| *A61K 9/08* | (2006.01) |
| *A61K 31/7004* | (2006.01) |
| *A61K 31/7068* | (2006.01) |
| *A61K 33/24* | (2019.01) |
| *A61K 38/06* | (2006.01) |
| *A61K 38/13* | (2006.01) |
| *A61K 38/28* | (2006.01) |
| *G01N 33/58* | (2006.01) |

(52) U.S. Cl.
CPC ........... *A61K 47/60* (2017.08); *A61K 9/08* (2013.01); *A61K 31/198* (2013.01); *A61K 31/337* (2013.01); *A61K 31/352* (2013.01); *A61K 31/585* (2013.01); *A61K 31/7004* (2013.01); *A61K 31/7068* (2013.01); *A61K 33/24* (2013.01); *A61K 38/06* (2013.01); *A61K 38/13* (2013.01); *A61K 38/28* (2013.01); *A61K 47/593* (2017.08); *A61K 47/6925* (2017.08); *C08G 63/664* (2013.01); *C08G 63/6852* (2013.01); *C08G 63/912* (2013.01); *G01N 33/582* (2013.01); *C08G 2230/00* (2013.01)

(58) Field of Classification Search
None
See application file for complete search history.

(56) References Cited

U.S. PATENT DOCUMENTS

2003/0068377 A1   4/2003   Fowers et al.
2010/0260743 A1   10/2010  Diwan et al.
2013/0331526 A1*  12/2013  Kim

OTHER PUBLICATIONS

Ankola et al. (Macromolecules, published 2009, pp. 7388-7395) (Year: 2009).*
Solimando et al. (Journal of Bioactive and Compatible Polymers, published 2014, pp. 330-349) (Year: 2014).*
Lapi et al. (Journal of Polymer Science, published 2012, pp. 3800-3809) (Year: 2012).*

* cited by examiner

*Primary Examiner* — Alma Pipic
(74) *Attorney, Agent, or Firm* — Winstead PC (57) ABSTRACT

The present invention provides a biodegradable "precision polymer system" (poly system) and methods for preparing pharmaceutically effective "precision polymer nanosystems" (polymer nanosystem) for delivery and/or targeting of drugs or drug like compounds.

12 Claims, 4 Drawing Sheets

POLYMER SYSTEMS AND THEIR APPLICATIONS IN DIAGNOSTICS AND DRUG DELIVERY

CROSS-REFERENCES TO RELATED APPLICATIONS

This application claims the benefit under 35 U.S.C. § 119(e) of U.S. Provisional Patent Application No. 62/149,563, filed Apr. 18, 2015, which is incorporated herein by reference in its entirety as if fully set forth herein.

FIELD OF THE INVENTION

The present invention provides a biodegradable polymer system and methods for preparing pharmaceutically effective polymer nanosystems for delivery and/or targeting of drugs or drug like compounds.

BACKGROUND OF THE INVENTION

Biodegradable polymers have been used as surgical sutures, wound dressings, and as drug delivery systems. Among them, polylactide (PLA), polyglycolide (PGA) and their copolymers (PLGA) have attracted the most attention.

Currently there are few synthetic or natural polymeric materials that can be used for the controlled and targeted delivery of drugs, including peptide and protein drugs, because of strict regulatory compliance requirements such as biocompatibility, low toxicity, having a clearly defined degradation pathway, and safety of the polymers and degradation products. The most widely investigated and advanced biodegradable polymers in regard to available toxicological and clinical data are the aliphatic poly($\alpha$-hydroxy acids), such as poly(D-, L-, or D, L-lactic acid) (PLA) with varying stereochemistry (L, D or DL), poly(glycolic acid) (PGA) and their copolymers (PLGA). These polymers are commercially available and are presently used as bioresorbable sutures and in biodegradable microsphere drug delivery systems.

Even though there has been some success, the success at large is limited by the inability of the commercially available polymers as platforms for wide variety of drugs with distinct physicochemical attributes eg solubility, molecular weight, permeability. Additionally, currently known copolymer-based drug carriers do not exhibit efficient targeted delivery of drug compositions.

Thus, it would be beneficial to have a polymer system that have the ability to optimize ligand-receptor stoichiometry facilitating a receptor-specific targeted delivery combined with tunable release property and further lends itself to facilitate the delivery of compounds with distinct physicochemical attributes.

SUMMARY OF THE INVENTION

The present invention provides biodegradable polymer system compositions and methods for preparing a pharmaceutically effective polymer nanosystems for delivery and/or targeting of drugs or drug like compounds.

The present invention also provides a method for preparing the biodegradable drug delivery composition and a method for effectively administering such a composition to whole body systems eg animals, humans. The drug delivery composition of the present invention can be administered without an aqueous vehicle, or can be administered after being reconstituted in an aqueous vehicle to afford a stable suspension. The administration can be done by peroral means. Additionally, the drug compositions may be administered via the nose or skin and can be injectable.

The present invention describes a novel biodegradable polymer system compositions and methods for preparing pharmaceutically effective polymer nanosystems for delivery of drugs or drug like compounds precisely where it is needed in the body with minimal non-target effects. Embodiments of the invention are directed to creating biodegradable repeating units with a specific biological function that can form polymer nanosystem with defined size and function e.g., improve intestinal uptake of the polymer nanosystem containing bioactive(s) and/or direct them to a specific site of action to deliver the pay load e.g., tumor epithelium or inflamed endothelium or a specific organ of interest. These polymer systems/polymer nanosystems go beyond the current available systems in that they allow optimization of ligand-receptor stoichiometry which is the key to achieve ideal receptor mediated delivery of the bioactives. Most nanomedicines that are currently under development are single bioactive based. However, the polymer nanosystems allow a combination of bioactives, where such systems are advantageous in the treatment of several diseases e.g., diabetes, cancer, cardiovascular. These systems offers flexibility of converting the molecules that are administered by injections to orally/peroral viable medicines, and can avoid refrigerated storage. These polymer systems/polymer nanosystems can serve as a platform technology for a variety of bioactives and diseases in that, the bioactive(s) encapsulated and the surface ligands specific to receptor can be varied in a manner that suits a disease of interest. These polymer nanosystems can be designed such a way by varying the molecular weight of the building blocks so that the encapsulated bioactive(s) are released over several days. These polymer nanosystems can be appropriately tailored making them route independent, in that they can be administered via mouth, nose, skin or can be injectable. These polymer nanosystems can be ideal for existing bioactives to improve their performance as well as for new indications.

The composition of the present invention comprises: 1) one or more biodegradable block copolymer drug carriers comprising A-B, A-B-A or B-A-B block, with chain linkers imparting periodic pendent carboxyl or amine functional groups throughout the polymer backbone, wherein the A block is a biodegradable polyester and the B block is polyethylene glycol (PEG) with the weight percentage of the A block is between 1% to 99%; and chain linker is an aromatic or aliphatic tetracarboxylic dianhydride and 2) a polyethylene glycol (PEG), a PEG derivative, or a mixtures of PEG and a PEG derivative.

Examples of suitable biodegradable polymers includes ABA- or BAB-type triblock copolymers, or AB-type diblock copolymers based on biodegradable polyester A-blocks and hydrophilic B polymer block(s) consisting of polyethylene glycol (PEG). The biodegradable polyesters are synthesized from monomers selected from the group consisting of D,L-lactide, D-lactide, L-lactide, D,L-lactic acid, D-lactic acid, L-lactic acid, glycolide, glycolic acid, ε-caprolactone, 1,4-dioxan-2-one, ε-hydroxy hexanoic acid, γ-butyrolactone, γ-hydroxy butyric acid, δ-valerolactone, δ-hydroxy valeric acid, hydroxybutyric acids, malic acid, and copolymers thereof. Polyethylene glycol (PEG) is also sometimes referred to as poly(ethylene oxide) (PEO) or poly(oxyethylene) and the terms can be used interchangeably for the purposes of this invention.

The biodegradable block copolymer drug carriers suitable for the present invention can form homogeneous suspensions in an aqueous or any other suitable vehicle as desired. Homogeneous suspensions of the drug delivery compositions include all flowing forms of the compositions of the present invention, with or without water, drug(s), and any additives or excipients as necessary to prepare formulations that are pharmaceutically and therapeutically useful. The drug may be present as either a true solution or in a colloidal state such as emulsion or a suspension. All forms can act to facilitate administration of the drug and enhance the therapeutic effect. Such therapeutic effects may be optimized by controlling the copolymer molecular weights, compositions, and the relative ratios of the hydrophilic and hydrophobic blocks, ratios of drug to copolymer, ratios of copolymer to PEG and/or PEG derivatives, concentration of the conjugated ligands to pendent carboxyl or amine functional groups, the particle size and both drug and copolymer concentrations in the final administered dosage form. Additional advantages of this invention will become apparent from the following detailed description of the various embodiments.

DETAILED DESCRIPTION OF EXEMPLARY EMBODIMENTS

"Biodegradable" means that the block copolymer or oligomer can chemically break down or degrade within the body to form nontoxic components. The rate of degradation can be the same or different from the rate of drug release.

"Drug" shall mean any organic or inorganic compound or substance having biological or pharmacological activity that can be adapted or used for a therapeutic purpose.

"Peptide," "polypeptide," "oligopeptide" and "protein" shall be used interchangeably when referring to peptide or protein drugs and shall not be limited as to any particular molecular weight, peptide sequence or length, field of bioactivity or therapeutic use unless specifically stated.

"PLA" shall mean a polymer derived from the polycondensation of lactic acid or by the ring opening polymerization of lactide.

"Biodegradable polyester refers to any polymer preferably synthesized from monomers selected from the group consisting of D,L-lactide, D-lactide, L-lactide, D,L-lactic acid, D-lactic acid, L-lactic acid, glycolide, glycolic acid, ε-caprolactone, 1,4-dioxan-2-one, ε-hydroxy hexanoic acid, γ-butyrolactone, γ-hydroxy butyric acid, δ-valerolactone, δ-hydroxy valeric acid, hydroxybutyric acid, malic acid, ethyleneglycol and mixtures thereof.

In one embodiment, the biodegradable polymer system comprises ABA-type or BAB-type triblock copolymers, AB-type diblock copolymers or mixtures thereof, where the A-blocks are relatively hydrophobic and comprises a biodegradable polyester, and the B-blocks are relatively hydrophilic and comprises polyethylene glycol (PEG).

In another embodiment, the biodegradable polymer system comprises multiblock ABA- or BAB-type copolymers of lactic acid and ethylene glycol with periodically spaced side chain carboxyl groups. Multiple pendent carboxyl groups are imparted into the PLA-PEG backbone via the incorporation of an aromatic or aliphatic tetracarboxylic anhydride moiety in the chain extension step. In certain embodiments of the invention, the tetracarboxylic dianhydrides that are used are pyromellitic dianhydride and cyclohexane tetracarboxylic dianhydride.

In addition, an embodiment of the present invention is directed to a variation of polymer system that is synthesized with a diamine linker conjugated to the carboxyl groups, such that one of the amine moieties of the linker is covalently bonded to the carboxyl of the polymer while the other remains free for conjugating ligands. The two variations of the polymer, with free carboxyl and amine unit, provides the flexibility to attach the ligands with either a free hydroxyl, amine or carboxyl functionality respectively, without the need of any further alteration of either the polymer or ligand.

As proof of concept some embodiments of the present invention, have been synthesized with PLA and PEG blocks and aromatic or aliphatic linkers imparting multiple pendent carboxyl groups in the polymer backbone. The polymers are characterized using nuclear magnetic resonance (NMR) and gel permeation chromatography (GPC) to verify their chemistry and evaluate their molecular weight. As described above, carboxyl groups for certain embodiments of invention are capped with diamine moieties. Both the variations of polymer nanosystem, with pendent carboxyl and amine groups are further conjugated to ligands with free reactive hydroxyl, amine or carboxyl functionalities. Polymers thus obtained can be used to form polymer nanosystem by appropriate methods. The X-ray photoelectron spectroscopy (XPS) analysis performed on the polymer nanosystem shows that the ligands attached to the polymer system are displayed on the surface of the polymer nanosystem, which is imperative for their availability for binding to the respective receptors on the cells.

The PEG, PEG derivatives or mixtures thereof used in the present invention dissolves or uniformly mixes with the biodegradable block copolymer and so reduces the viscosity and increases the fluidity of the composition. The compositions of the present invention are flowable liquids or can be easily formulated with an aqueous vehicle to afford a homogeneous uniform colloidal system. The composition can be easily administered as is or reconstituted with an aqueous or appropriate vehicle. After the administration, the block copolymer drug carrier may or may not form a drug depot. Therefore, the liquid PEG, PEG derivative or mixtures thereof of the present invention should be a material that does not cause loss of activity of the physiologically active substance.

Drugs that may be incorporated with the drug delivery compositions of the present invention can be any bioactive agent, but particular advantage is achieved with bioactive agents having limited solubility or dispersibility in an aqueous or hydrophilic environment, or any bioactive agent that requires enhanced solubility or permeability. In addition, the choice of ligand conjugated to the polymer system will play an important role in the absorption and targetability of the polymer nanosystem and encapsulated drugs, thus enhancing their site/target specificity.

The present invention thus provides compositions comprising biodegradable block copolymer drug carriers and PEG, PEG derivatives or mixtures thereof that are powders or can be rapidly reconstituted in an aqueous vehicle to afford useful forms that are uniform colloidal systems. The drug solution formed with the drug delivery compositions of the present invention has desirable physical stability, therapeutic efficacy, and toxicology. The PEG, PEG derivatives or mixtures thereof of the present invention can be used for water soluble or water insoluble block copolymeric drug carriers, particularly for biodegradable di- or triblock copolymers that have reverse gelation properties and/or polymers that can enhance the solubility of drugs, especially hydrophobic drugs.

WORKING EXAMPLES

Abbreviations $CH_2Cl_2$ Methylene Chloride
DIEA N,N-diisoethylpropylamine
DMAB Didodecyldimethylammonium bromide
DMAP 4-Dimethylaminopyridine
DMF N,N-dimethylformamide
EDA Ethylenediamine
EDC 1-Ethyl-3-(3-dimethylaminopropyl) carbodiimide
GA Gambogic acid
GaL Galactose
RGD Arginylglycylaspartic acid
PVA Poly(vinyl alcohol)
TFA Trifluoroacetic acid
TfR Transferrin receptor
TPGS D-α-Tocopheryl polyethylene glycol 1000 succinate
NS Nanosystems
P2s Precision polymers
PLGA Polylactide-co-glycolide
P2Ns Ligand functional precision polymer nanosystems Example 1

This example describes the synthesis of PLA-PEG400 block pre-polymer from 1-lactide and 7% (w/w) PEG-400.

A 250 ml three necked round-bottomed flask fitted with a reflux condenser, magnetic stirrer, heat-on-block and under a gentle purge of nitrogen, was charged with 1-Lactide (18.0 g; 0.125 mol), PEG400 (3.52 g; 2.65 ml; 0.0088 mol), Stannous Octoate (21.52 mg; 17.20 µl; 0.1% w/w), Toluene (50 ml). The reaction mixture was heated to a temperature of 115° C. while stirring to allow the solvent to reflux. The reaction was carried out under these conditions for 24 h, after which reaction mixture was cooled and solvent was evaporated under reduced pressure. The residue left upon evaporation of solvent was dissolved in 12 ml methylene chloride and precipitated in 400 ml cold diethyl ether under vigorous stirring. The white polymer was obtained by filtration under suction and dried under vacuum to a constant dry weight (16 mg).

Example 2

This example describes the chain extension of the pre-polymer from example 1 with the incorporation of an aromatic linker to impart multifunctionality.

A 250 ml three necked round-bottomed flask fitted with a reflux condenser, magnetic stirrer, heat-on-block and under a gentle purge of nitrogen was charged with PLA-PEG400 (7 g; 0.6364 mmol), Pyromellitic dianhydride (166.56 mg; 0.7636 mmol), Triethylamine (128.81 mg; 177.42 µl; 1.2728 mol), Stannous Octotate (7 mg; 5.6 µl; 0.1 w/w) and Toluene (40 ml). The reaction mixture was heated to a temperature of 115° C. while stirring to allow the solvent to reflux. The reaction was carried out under these conditions for 24 h, after which reaction mixture was cooled and solvent was evaporated under reduced pressure. The residue dissolved in 10 ml methylene chloride and precipitated in 500 ml cold diethyl ether under vigorous stirring. The white polymer was collected by filtration under suction and dried under vacuum to a constant dry weight (6.2 g).

Example 3

This example describes the chain extension of the pre-polymer from example 1 with the incorporation of an aliphatic linker to impart multifunctionality.

A 250 ml three necked round-bottomed flask fitted with a reflux condenser, magnetic stirrer, heat-on-block and under a gentle purge of nitrogen, was charged with PLA-PEG400 (8 g; 0.7273 mmol), Cyclohexane tetracarboxylic dianhydride (195.66 mg; 0.8728 mmol), Triethylamine (147.25 mg; 202.82 µl; 1.455 mmol), Stannous Octoate (8 mg; 6.4 µl; 0.1% w/w) and Toluene (50 ml). The reaction mixture was heated to a temperature of 115° C. while stirring to allow the solvent to reflux. The reaction was carried out under these conditions for 24 h, after which reaction mixture was cooled and solvent was evaporated under reduced pressure. The residue dissolved in 10 ml methylene chloride and precipitated in 400 ml cold diethyl ether under vigorous stirring. The white polymer was collected by filtration under suction and dried under vacuum to a constant dry weight (6.1 g).

Example 4

This examples describes the synthetic process of the aminated version of hP2-400 (hP2-400-EDA) described in example 3 using EDA.

A 50 ml three necked round bottomed flask equipped with magnetic stirrer and under a gentle purge of nitrogen was charged with hP2-400 (250 mg; 0.0142 mmol; 11 COOH/mol), EDC (40.83 mg; 0.2131 mmol) and DMF (3 ml) and stirred at room temperature for 30 min. n-boc-EDA (34.12 mg; 33.72 µl; 0.213 mmol) and DIEA (27.53 mg; 37.1 µl) were subsequently added to the sitting solution and the reaction was continued for 18 h. The polymer was obtained by precipitation after pouting the reaction mixture in cold water. The precipitate was washed twice with water and dried under vacuum. The dried polymer was dissolved in 2.2 ml of 10:1 mixture of CH2Cl2:TFA and stirred at room temperature for 1 h under nitrogen atmosphere. The solvent was then stripped off on a rotary evaporator and product washed with water to get a white polymer. The hP2-400-EDA polymer was dried under vacuum to a constant dry weight (195 mg).

Example 5

This examples describes synthesis process of the thioester version of pP2-400 described in example 2 using 2-mercaptoethanol.

A 50 ml three necked round bottomed flask equipped with magnetic stirrer, condenser and a heat-on block, and under a gentle purge of nitrogen was charged with pP2-400 (100 mg; 0.011 mmol; 13 COOH/mol), 2-mercaptoethanol (12.89 mg; 11.61 µl; 0.165 mmol), methanesulfonic acid (15.86 mg; 10.71 µl; 0.165 mmol) and DMF (2 ml). The reaction mixture was stirred at 100° C. for 24 h, after which the product was obtained by precipitation in cold water. The product was further washed four times with water until the sulfur smell was eliminated and dried under vacuum to a constant dry weight (57.7 mg).

Example 6

This examples describes the conjugation of Gambogic acid to the aminated hP2-400 described in example 4.

A 50 ml three necked round bottomed flask equipped with magnetic stirrer and under a gentle purge of nitrogen was charged with gambogic acid (65.2 mg; 0.1037 mmol), EDC (29.83 mg; 0.1556 mmol) and CH2Cl2 (1 ml) and stirred at ambient temperature for 30 min hP2-400-EDA (125 mg; 0.0069 mmol) pre-dissolved in CH2Cl2 (2 ml) and DIEA (20.11 mg; 27.1 µl; 0.1556 mmol) were subsequently added to the stirring solution and the reaction was carried out at these conditions for another 18 h. The product was obtained by precipitation in cold ether. The polymer was further washed one with ether and another time with water and dried under vacuum to a constant dry weight (104 mg).

Example 7

This example describes the conjugation of Galactose to hP2-400 described in example 3.

A 50 ml three necked round bottomed flask equipped with magnetic stirrer and a heat-on block, and under a gentle purge of nitrogen was charged with hP2-400 (250 mg; 0.0142 mmol; 11 COOH/mol), D-galactose (38.39 mg; 0.2131 mmol), methanesulfonic acid (20.48 mg; 13.83 µl; 0.2131 mmol) and DMF (3 ml). The reaction mixture was stirred at 60° C. for 24 h, after which the product was obtained by precipitation in cold water. The product was further washed twice with water and dried under vacuum to a constant dry weight (242.1 mg).

Example 8

This example describes the conjugation of arginylglycylaspartic acid (RGD peptide) to hP2-400 described in example 3.

A 50 ml three necked round bottomed flask equipped with magnetic stirrer and under a gentle purge of nitrogen was charged with hP2-400 (150 mg; 0.0085 mmol; 11 COOH/mol), EDC (24.44 mg; 0.1275 mmol) and DMF (2 ml) and stirred at room temperature for 30 min RGD (44.16 mg; 0.1275 mmol) pre-dissolved in 1 ml DMF and DIEA (16.48 mg; 22.21 µl; 0.1275 mmol) were subsequently added to the stirring solution and the reaction was continued at these conditions for 18 h. The product was obtained by precipitation in cold water. The polymer was further washed twice in water and dried under vacuum to a constant dry weight (122 mg).

Example 9

This example describes the conjugation of fluorescent probe, Fluorescein to aminated hP2-400 described in example 4.

A 50 ml three necked round bottomed flask equipped with magnetic stirrer and under a gentle purge of nitrogen was charged with hP2-400-EDA (25 mg; 0.00128 mmol; 9 NH2/mol), NHS-Fluorescein (7.24 mg; 0.0153 mmol), DIEA (1.98 mg; 2.7 µl; 0.0153 mmol) and DMF (1 ml). The reaction mixture was stirred in dark under inert atmosphere for 18 h. The product was obtained by precipitation in cold water. The polymer was further washed twice in water and dried under vacuum to a constant dry weight (12.5 mg).

Example 10

This example describes the conjugation of Hesperetin to pP2-400 described in example 2.

A 50 ml three necked round bottomed flask equipped with magnetic stirrer and under a gentle purge of nitrogen was charged with pP2-400 (100 mg; 0.0105 mmol; 11 COOH/mol), EDC (30.19 mg; 0.1575 mmol) and DMF (1 ml) and stirred at room temperature for 30 min. Hesperetin (47.61 mg; 0.1575 mmol) and DMAP (1.92 mg; 0.01575 mmol) pre-dissolved in 1 ml DMF were subsequently added to the stirring solution and the reaction was continued at these conditions for 18 h. The product was obtained by precipitation in cold water. The polymer was further washed twice and dried under vacuum to a constant dry weight.

Example 11

This example describes the conjugation of 1-Lysine to pP2-400 described in example 2.

A 50 ml three necked round bottom flask equipped with a magnetic stirrer and under a gentle purge of nitrogen was charged with pP2-400 (100 mg; 0.1 mmol; 11 COOH/mol), EDC (28.75 mg; 0.15 mmol) and DMF (0.5 ml) and stirred at ambient temperature for 30 min 1-Lysine (21.93 mg; 0.15 mmol) predissolved in DMF (0.5 ml) and DIEA (19.39 mg; 26.13 µl; 0.15 mmol) were subsequently added to the reaction flask and the reaction was carried out under nitrogen atmosphere and room temperature for 18 h. A pale yellow product was obtained by precipitation in water. The polymer was further washed twice with water and dried under vacuum to a constant dry weight (82.9 mg).

Example 12

This example describes the conjugation of Cysteine to pP2-400 described in example 2.

A 50 ml three necked round bottom flask equipped with a magnetic stirrer and under a gentle purge of nitrogen was charged with pP2-400 (100 mg; 0.1 mmol; 11 COOH/mol), EDC (28.75 mg; 0.15 mmol) and DMF (0.5 ml) and stirred at ambient temperature for 30 min. Cysteine (18.17 mg; 0.15 mmol) predissolved in DMF (0.5 ml) and DIEA (19.39 mg; 26.13 µl; 0.15 mmol) were subsequently added to the reaction flask and the reaction was carried out under nitrogen atmosphere and room temperature for 18 h. A pale yellow polymer was obtained by precipitation in water. The polymer was further washed twice with water and dried under vacuum to a constant dry weight (65.1 mg).

Example 13

This example describes the conjugation of Arginine to pP2-400 described in example 2.

A 50 ml three necked round bottom flask equipped with a magnetic stirrer and under a gentle purge of nitrogen was charged with pP2-400 (100 mg; 0.1 mmol; 11 COOH/mol), EDC (28.75 mg; 0.15 mmol) and DMF (0.5 ml) and stirred at ambient temperature for 30 min 1-Arginine (26.13 mg; 0.15 mmol) predissolved in DMF (0.5 ml) and DIEA (19.39 mg; 26.13 µl; 0.15 mmol) were subsequently added to the reaction flask and the reaction was carried out under nitrogen atmosphere and room temperature for 18 h. A pale yellow polymer was obtained by precipitation in water. The polymer was further washed twice with water and dried under vacuum to a constant dry weight (87.6 mg).

Example 14

This example describes the conjugation of Paclitaxel to pP2-400 described in example 2.

A 50 ml three necked round bottomed flask equipped with magnetic stirrer and under a gentle purge of nitrogen was charged with pP2-400 (100 mg; 0.0072 mmol; 10 COOH/mol), EDC (20.70 mg; 0.108 mmol) and DMF (0.5 ml) and stirred at room temperature for 30 min. Paclitaxel (92.2 mg; 0.108 mmol) and DMAP (1.32 mg; 0.0108 mmol) pre-dissolved in 0.5 ml DMF were subsequently added to the stirring solution and the reaction was continued at these conditions for 18 h. The product was obtained by precipitation in cold 1:1 mixture of ethanol and ethyl ether. The polymer was further washed twice and dried under vacuum to a constant dry weight (75 mg).

Example 15

This example describes the conjugation of Paclitaxel to hP2-400 described in example 3.

A 50 ml three necked round bottomed flask equipped with magnetic stirrer and under a gentle purge of nitrogen was charged with hP2-400 (100 mg; 0.00521 mmol; 9 COOH/mol), EDC (11.98 mg; 0.0625 mmol) and DMF (0.5 ml) and stirred at room temperature for 30 min. Paclitaxel (53.37 mg; 0.0625 mmol) and DMAP (0.76 mg; 0.00625 mmol) pre-dissolved in 0.5 ml DMF were subsequently added to the stirring solution and the reaction was continued at these conditions for 18 h. The product was obtained by precipitation in cold 1:1 mixture of ethanol and ethyl ether. The polymer was further washed twice and dried under vacuum to a constant dry weight (75 mg).

Example 16

This example describes the conjugation of Cisplatin to hP2-400 described in example 2.

A 50 ml three necked round bottom flask equipped with a magnetic stirrer and under a gentle purge of nitrogen was charged with pP2-400 (100 mg; 0.1 mmol; 8 COOH/mol), EDC (19.71 mg; 0.1 mmol) and DMF (1 ml) and stirred at ambient temperature for 30 min. Cisplatin (30 mg; 0.1 mmol) predissolved in DMF (1 ml) and DIEA (12.92 mg; 17.42 µl; 0.1 mmol) were subsequently added to the reaction flask and the reaction was carried out in the dark under nitrogen atmosphere and room temperature for 24 h. A yellow conjugated polymer was obtained by precipitation in water. The polymer was further washed twice with water and dried under vacuum to a constant dry weight (84.3 mg).

Example 17

This example describes the conjugation of Gemcitabine to pP2-400 described in example 2.

A 50 ml three necked round bottom flask equipped with a magnetic stirrer and under a gentle purge of nitrogen was charged with pP2-400 (100 mg; 0.1 mmol; 8 COOH/mol), EDC (19.71 mg; 0.1 mmol) and DMF (1 ml) and stirred at ambient temperature for 30 min. Gemcitabine (26.32 mg; 0.1 mmol) predissolved in DMF (1 ml) and DIEA (12.92 mg; 17.42 µl; 0.1 mmol) were subsequently added to the reaction flask and the reaction was carried out in the dark under nitrogen atmosphere and room temperature for 24 h. A yellow conjugated polymer was obtained by precipitation in water. The polymer further washed twice with water and dried under vacuum to a constant dry weight (80.6 mg).

Example 18

This example describes the conjugation of Withaferin A to pP2-2000H (A variation of pP2-400 described in example 2 with 2000 g/mol PEG chains and higher lactide concentration per chain of final polymer).

A 50 ml three necked round bottomed flask equipped with magnetic stirrer and under a gentle purge of nitrogen was charged with pP2-2000H (50 mg; 0.0017 mmol; 7 COOH/mol), EDC (3.26 mg; 0.017 mmol) and DMF (1 ml) and stirred at room temperature for 30 min. Withaferin A (8.0 mg; 0.017 mmol) and DMAP (0.21 mg; 0.0017 mmol) pre-dissolved in 1 ml DMF were subsequently added to the stirring solution and the reaction was continued at these conditions for 18 h. The product was obtained by precipitation in cold water. The polymer was further washed twice and dried under vacuum to a constant dry weight.

Example 19

This example describes the conjugation of diagnostic agents to P2s.

P2s can be functionalized with diagnostic agents e.g. MRI and ultrasound contrast agents, Near-IR fluorescent agents etc. by coupling them to the carboxyl or amine functionality of the P2s via ester or amide bonds based on the available functional unit of the agent. Both the processes involve activation of carboxyl on either the polymer or the diagnostic moiety by EDC followed by either amination in the presence of DIEA or esterification in the presence of DMAP. Alternatively, Fischer esterification can be employed to conjugate a moiety with hydroxyl functionality to the carboxylated P2, if the said moiety can withstand higher temperatures and strong acid catalyst.

Example 20

This example describes the use of P2s for coupling moieties of different functionalities.

Figure 1A:
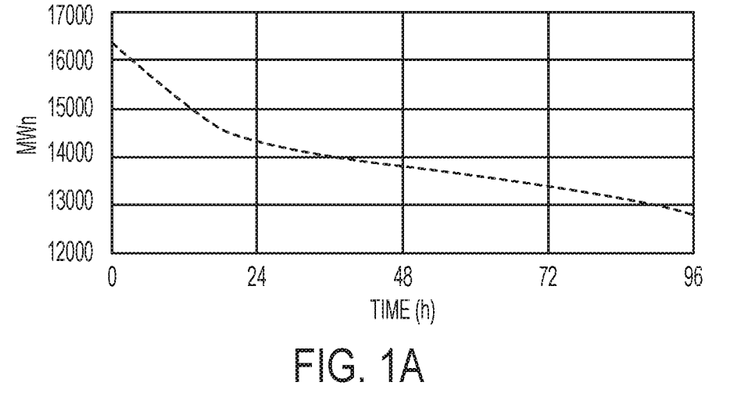
FIG. 1A shows the decrease in molecular weight of hP2-400 over a period of 96 hours in PBS at 37° C.
Figure 1B:
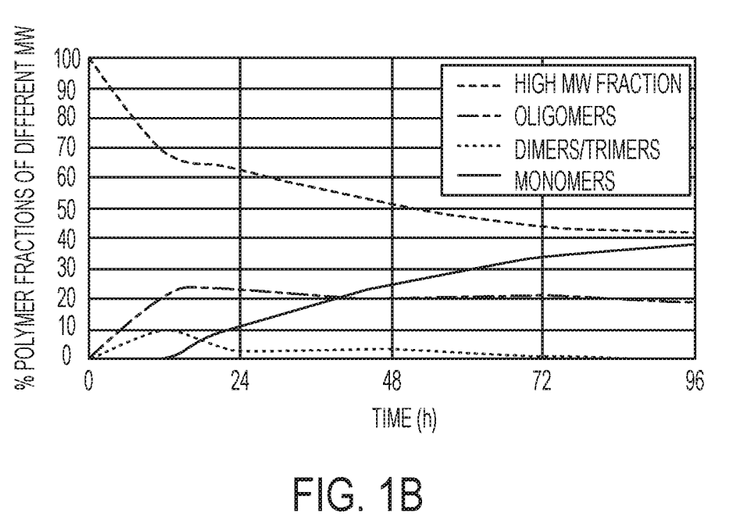
FIG. 1B shows the degradation profile of hP2-400 over a period of 96 hours in PBS at 37° C.
Figure 1C:
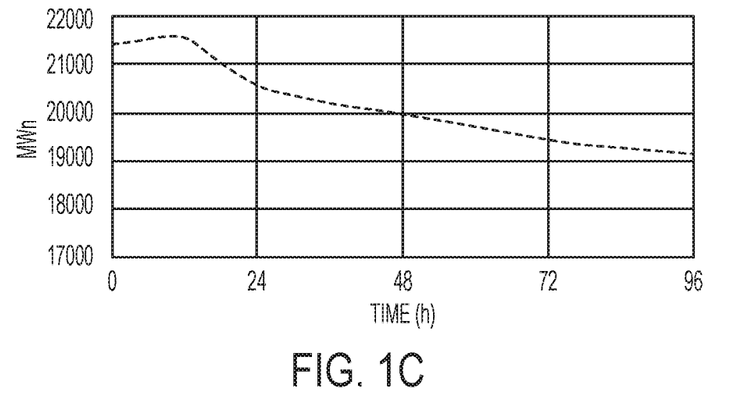
FIG. 1C shows the decrease in molecular weight of hP2-1000H over a period of 96 hours in PBS at 37° C.
Figure 1D:
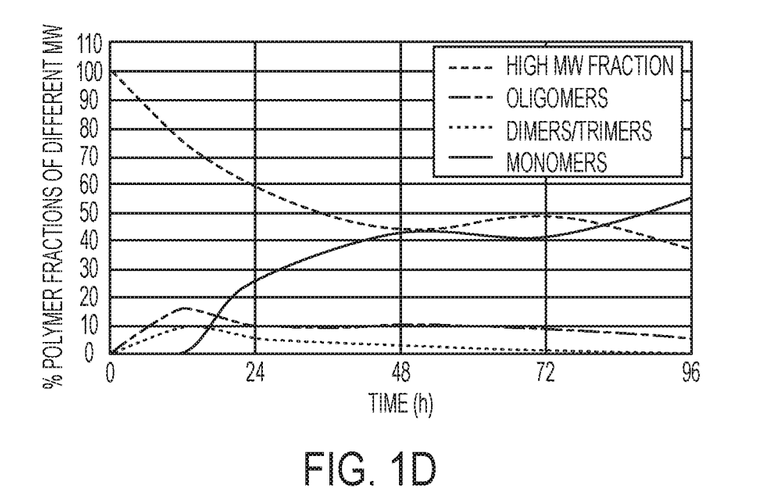
FIG. 1D shows the degradation profile of hP2-1000H over a period of 96 hours in PBS at 37° C.
Figure 1E:
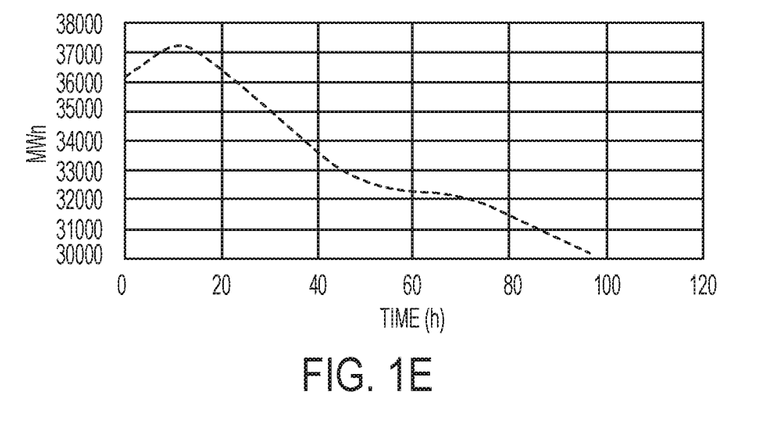
FIG. 1E shows the decrease in molecular weight of hP2-2000H over a period of 96 hours in PBS at 37° C.
Figure 1F:
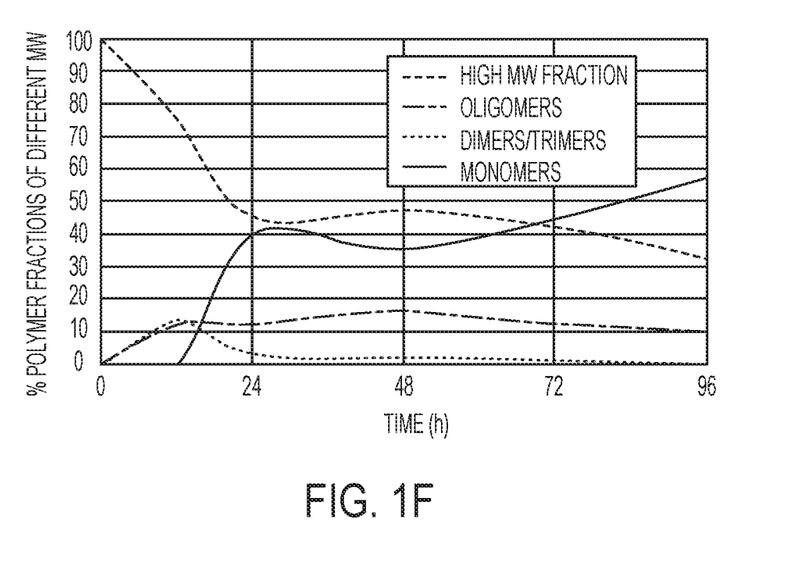
FIG. 1F shows the degradation profile of hP2-2000H over a period of 96 hours in PBS at 37° C.

The methods described in examples 4-19 can be employed on any and all P2s listed in table 3. All P2s can be aminated or thiolated and coupled to ligands, labeling and diagnostic agents, drug molecules etc. as described for the model P2s in the above mentioned examples. The choice of polymer is subject to the requirements for the end product in terms of level of multifunctionality, molecular weight and degradation profile. FIG. 1A shows the decrease in molecular weight of hP2-400 and FIG. 1B shows the degradation profile of hP2-400 over a period of 96 hours. FIG. 1C shows the decrease in molecular weight of hP2-1000H and FIG. 1D shows the degradation profile of hP2-1000H over a period of 96 hours. FIG. 1E shows the decrease in molecular weight of hP2-2000H and FIG. 1F shows the degradation profile of hP2-2000H over a period of 96 hours.

Example 21

This example describes the general preparation of NS of P2s.

Due to the multifunctional nature of P2s, large amount of ligand molecules can be attached to the polymer chains resulting in an increase in weight without the increase in chain length. To compensate for the lower level of backbone polymer available in conjugated polymers, additional plain P2s are added equal to the amount of ligand available on the polymer. To prepare NS, 25 mg of P2s or conjugated P2s (with additional plain P2s equal to cumulative ligand weight) were solubilized in 1.25 ml (2% w/v) mixture of CH2Cl2 and Ethyl acetate (based on their solubility; tablet) and emulsified in a 2.5 ml (0.1-2% w/v) solution of a stabilizer like DMAB, PVA, TPGS or a combination of the stabilizers. The emulsion was stirred at 1500 rpm for 5 min followed by homogenization at 15000 rpm for 7 min. The final emulsion was diluted with 10 ml water and stirred at 1000 rpm for 3 h. The NS were collected by centrifugation at 15000-20000×g at 4° C. for 30 minutes. The pellets of NS were suspended in 0.5 ml 5% (w/v) solution of trehalose dehydrate in water and freeze dried. The emulsification process can be modified based on the physico-chemistry of different drugs to be encapsulated to maximize entrapment efficiency.

Example 22

This example described the preparation of fluorescent P2Ns from hP2-400, hP2-400-GA, hP2-400-Gal and hP2-400-RGD described in examples 3, 6, 7 and 8 with incorporation of hP2-400-fluoroscein described in example 9.

Due to the multifunctional nature of hP2-400, large amount of ligand molecules can be attached to the polymer chains resulting in an increase in weight without the increase in chain length. To compensate for the lower level of backbone polymer available in conjugated hP2-400, additional plain hP2-400 was added equal to the amount of ligand available on the polymer. To prepare NS, 25 mg of hP2-400 or conjugated hP2-400 (with additional plain polymer equal to cumulative ligand weight) were mixed with 1 mg hP2-400-fluorescein and the mixture was solubilized in 1.25 ml (2% w/v) in a 1:4 mixture of CH2Cl2 and ethyl acetate. The organic phase was emulsified in a 2.5 ml (1% or 0.5% w/v) solution of DMAB. The emulsion was stirred at 1500 rpm for 5 min followed by homogenization at 15000 rpm for 7 min. The final emulsion was diluted with 10 ml water and stirred at 100 rpm for 3 h. The NS were collected by centrifugation at 15000-20000×g at 4° C. for 30 minutes. The pellets of NS were suspended in 0.5 ml 5% (w/v) solution of trehalose dehydrate in water and freeze dried.

Example 23

This example describes the encapsulation of Paclitaxel in NS of P2s.

To prepare paclitaxel loaded NS, 50 mg P2s and paclitaxel (5, 10, 15 or 20% w/w based on loading amount) were solubilized in 5 ml mixture of CH2Cl2 and ethyl acetate (based on their solubility; table 1) and emulsified in a 5 ml (1% w/v) solution of DMAB. The emulsion was stirred at 1500 rpm for 5 min followed by homogenization at 15000 rpm for 5 min. The final emulation was diluted with 20 ml water and stirred at 1000 rpm for 3 h. The NS were collected by centrifugation at 15000×g at 4° C. for 30 minutes. The pellets of NS were suspended in 0.5 ml 5% (w/v) solution of trehalose dehydrate in water and freeze dried.

Example 24

This example describes the encapsulation of Insulin in NS of P2s.

Insulin loaded P2s-NS were prepared using a double emulsion technique. 50 mg P2s were dissolved in 3 ml mixture of CH2Cl2 and ethyl acetate (based on their solubility; tablet). Insulin was separately dissolved in 0.5 ml 1.5% (w/v) solution of PVA in 0.01M HCl in an amount equal to 5, 10 or 15% (w/w) of the polymer content based on intended loading. The aqueous phase containing insulin was emulsified in the organic phase containing polymer and stirred at 1500 rpm for 3 min this primary emulsion was then added to 10.5 ml 1.5% (w.v) PVA solution in water to form a secondary emulsion which was further stirred for 3 min at 1500 rpm. The emulsion was homogenized at 15000 rpm for 7 min followed by dilution in 20 ml water. The final suspension was stirred for 3 h at 1000 rpm to allow the organic solvent to diffuse out and evaporate. The NS were collected by centrifugation at 15000×g at 4° C. for 30 minutes. The pellets of NS were suspended in 0.5 ml 5% (w/v) solution of trehalose dehydrate in water and freeze dried.

Example 25

This example describes the encapsulation of Cyclosporine A in P2s_NS.

To prepare cyclosporine A loaded NS, 50 mg P2s and cyclosporine A (5, 10 or 15% w/w based on loading amount) were solubilized in 2.5 ml mixture of CH2Cl2 and Ethyl acetate (based on their solubility; table 1) and emulsified in a 5 ml (0.1% w/v) solution of DMAB. The emulsion was stirred at 1500 rpm for 1 min followed by probe sonication at 20% amplitude for 30 s. The final emulsion was diluted with 20 ml water and stirred at 1000 rpm for 3 h. The NS were collected by centrifugation at 15000×g at 4° C. for 30 minutes. The pellets of NS were suspended in 0.5 ml 5% (w/v) solution of trehalose dehydrate in water and freeze dried.

Example 26

This example describes the uptake of fluorescent P2Ns of hP2-400 described in example 22 in Caco-2 cells monolayers.

Freeze-dried fluorescent P2NS and PLGA NS (plain or conjugated to GA, Gal or RGD) were suspended in dH20 at a concentration of 50 and 250 μg/ml respectively. Caco-2 cells were incubated with the 200 μl of F-NS suspension for 5 min at 37° C./5% CO2, followed by addition serum free medium and further incubation for 1 h at 37° C./5% CO2. The cells were washed three times with phosphate buffered saline (PBS, pH 7.4) and further processed for fluorescent microscopy and FACS for uptake.

Example 27

This example describes the evaluation of non-competitive binding of fluorescent P2Ns-GA of hP2-400 described in example 22 to transferrin receptor (TfR) in Caco-2 cells monolayers.

The TfR on Caco-2 monolayers were blocked using human specific TfR primary antibody by incubating for 30 min at 37° C. in $CO_2$ incubator. After three consecutive washings with PBS, P2Ns-GA were added and incubated for further 1 h. These were then washed with PBS 3 times and trypsinized and subjected to FACS analysis.

Example 28

This example describes the uptake of fluorescent P2Ns of hP2-400 described in example 22 in ex vivo intestinal tissue.

To study the uptake of P2Ns in intestinal tissue, 4 μm cryosections of previously excised small intestine were treated with fluorescent plain or ligand conjugated P2Ns suspension in PBS. After 1 h incubation at 37° C., the sections were washed multiple times to remove unbound un-internalized NS followed by staining of actin and mounting with mountant containing DAPI.

Example 29

This example describes the evaluation of non-competitive binding of fluorescent P2Ns-GA of hP2-400 described in example 22 to transferrin receptor (TfR) in ex vivo small intestine tissue sections.

The TfR on 4 μm cryosections of previously excised small intestine were blocked using human/mouse specific TfR primary antibody by incubating for 30 min at 37° C. in $CO_2$ incubator. After three consecutive washings with PBS, P2Ns-GA were added and incubated for further 1 h. These were then washed with PBS 3 times and processed for microscopic evaluation.

Example 30

This example describes the kinetics of fluorescent P2Ns of hP2-400 described in example 22 in vivo in Sprague Dawley rats.

Figure 2A:
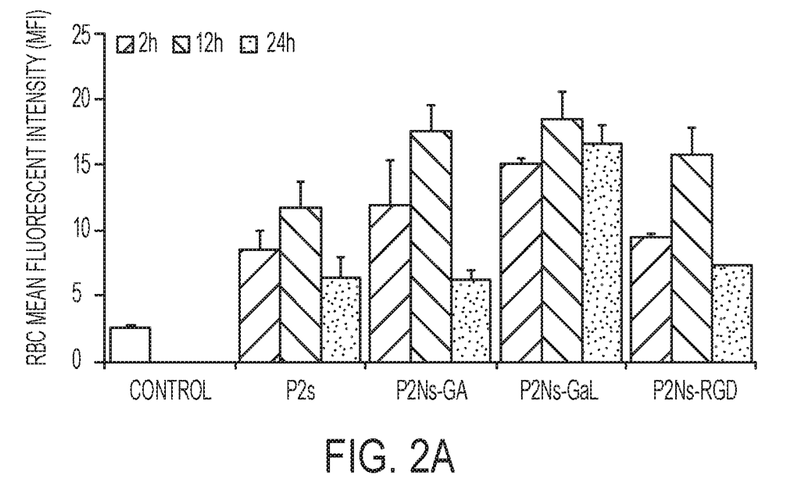
FIG. 2A shows the mean fluorescent intensity of fluorescent P2Ns of hP2-400 in RBCs.
Figure 2B:
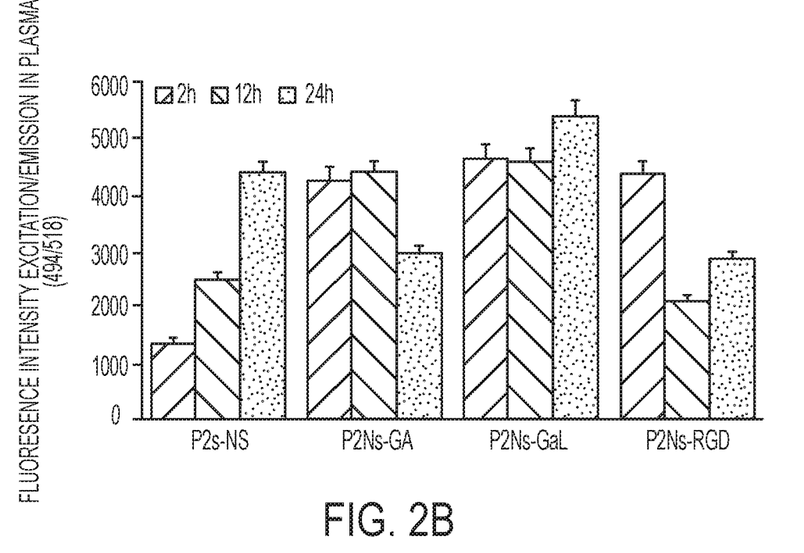
FIG. 2B shows the mean fluorescent intensity of fluorescent P2Ns of hP2-400 in plasma.

Male Sprague Dawley rats (300-320 g) were dosed perorally with fluorescent plain and conjugated P2Ns (16 mg/rat). Blood was collected via heart puncture at terminal sacrifice at 2, 12 and 24 h. Plasma and RBCs were processed for fluorescence quantification. The plasma kinetics shows ligand specific variable absorption, where those with no ligands were absorbed over extended periods of times suggesting they are lodged in the intestine. FIG. 2A shows the mean fluorescent intensity of fluorescent P2Ns of hP2-400 in RBCs. FIG. 2B shows the mean fluorescent intensity of fluorescent P2Ns of hP2-400 in plasma.

TABLE 1

Solubility of hP2s in mixture of methylene chloride and ethyl acetate

| Polymer | Ratio (methylene chloride:ethyl acetate) |
|---|---|
| hP2-400 | 1:4 |
| hP2-400LP | 1:4 |
| hP2-1000 | 2:3 |
| hP2-2000 | 3:2 |
| hP2-1000H | 1:4 |
| hP2-2000H | 1:4 |

TABLE 2

Molecular weighs and composition of different PLA-PEG prepolymers with varying chain lengths of PEG and ratios of lactide or lactic acid to ethylene glycol and the constituent PEG molecules

| Prepolymer | PEG Chain MW | Lactide:EG | LA:EG | Lactide:PEG | LA:PEG | MWn | MWw | PDI |
|---|---|---|---|---|---|---|---|---|
| PLA-PEG400 | 400 | 1.59 | 3.17 | 14.29 | 28.57 | 11000 | 13000 | 1.2 |
| PLA-PEG400LP | 400 | 3.17 | 6.35 | 28.57 | 57.14 | 16000 | 18200 | 1.1 |
| PLA-PEG1000 | 1000 | 0.65 | 1.30 | 14.29 | 28.57 | 5300 | 6100 | 1.2 |
| PLA-PEG2000 | 2000 | 0.32 | 0.63 | 14.29 | 28.57 | 8600 | 9500 | 1.1 |
| PLA-PEG1000H | 1000 | 1.59 | 3.18 | 34.98 | 69.96 | 16100 | 18300 | 1.1 |
| PLA-PEG2000H | 2000 | 1.59 | 3.18 | 71.55 | 143.10 | 18600 | 22000 | 1.2 |

TABLE 3

Range of P2s prepared by chain extending prepolymers from table 1 with their respective molecular weight profiles and mol/mol carboxyl side groups perdiosically placed along the polymer chains.

| Prepolymer | Polymer | Linker | MWn | MWw | PDI | mol/mol carboxyls |
|---|---|---|---|---|---|---|
| PLA-PEG400 | pP2-400 | PMDA | 15700 | 22300 | 1.4 | 7 |
|  | hP2-400 | HCDA | 19200 | 30900 | 1.6 | 9 |
| PLA-PEG400LP | pP2-400LP | PMDA | 27700 | 44300 | 1.6 | 10 |
|  | hP2-400LP | HCDA | 24500 | 37500 | 1.5 | 10 |
| PLA-PEG1000 | pP2-1000 | PMDA | 6000 | 7300 | 1.2 | 5 |
|  | hP2-1000 | HCDA | 9700 | 13800 | 1.4 | 6 |
| PLA-PEG2000 | pP2-2000 | PMDA | 11000 | 12700 | 1.2 | 8 |
|  | hP2-2000 | HCDA | 11700 | 14400 | 1.2 | 6 |
| PLA-PEG1000H | pP2-1000H | PMDA | 18100 | 22300 | 1.2 | 12 |
|  | hP2-1000H | HCDA | 19700 | 26100 | 1.3 | 12 |

TABLE 3-continued

Range of P2s prepared by chain extending prepolymers from table 1 with their respective molecular weight profiles and mol/mol carboxyl side groups perdiosically placed along the polymer chains.

| Prepolymer | Polymer | Linker | MWn | MWw | PDI | mol/mol carboxyls |
|---|---|---|---|---|---|---|
| PLA-PEG2000H | pP2-2000H | PMDA | 28800 | 38100 | 1.3 | 7 |
| | hP2-2000H | HCDA | 33000 | 44600 | 1.4 | 11 |

*PMDA: Pyromellitic dianhydride; HCDA: Cyclohexanetetracarboxylic dianhydride

TABLE 4

Particle size and entrapment efficiency of Paclitaxel in P2s-NS and conventional PLGA (for comparison)

| | 5% | | 10% | | 15% | | 20% | |
|---|---|---|---|---|---|---|---|---|
| Polymer | Size | % EE | Size | % EE | Size | % EE | Size | % EE |
| PLGA | 172 ± 15 | 51 ± 5 | The method failed to produce particles beyond 5% paclitaxel load | | | | | |
| hP2-400 | 146 ± 7 | 39 ± 3 | 117 ± 8 | 33 ± 4 | 145 ± 16 | 44 ± 3 | 124 ± 7 | 44 ± 4 |
| hP2-1000H | 114 ± 8 | 25 ± 5 | The method failed to produce particles beyond 5% paclitaxel load | | | | | |
| hP2-2000H | 170 ± 2 | 33 ± 6 | The method failed to produce particles beyond 5% paclitaxel load | | | | | |

TABLE 5

Particle size and entrapment efficiency of Insulin in P2s-NS and conventional PLGA (for comparison)

| | 5% | | 10% | | 15% | |
|---|---|---|---|---|---|---|
| Polymer | Size | % EE | Size | % EE | Size | % EE |
| PLGA | 249 ± 15 | 47 ± 5 | 264 ± 9 | 46 ± 2 | 262 ± 12 | 46 ± 6 |
| hP2-400 | 351 ± 25 | 37 ± 4 | 340 ± 23 | 48 ± 5 | 276 ± 12 | 62 ± 4 |
| hP2-2000H | 305 ± 56 | 10 ± 0.2 | 343 ± 10 | 12 ± 2 | 363 ± 10 | 7 ± 1 |

TABLE 6

Particle size and entrapment efficiency of Cyclosporine A in hP2-2000H

| | 5% | | 10% | | 15% | |
|---|---|---|---|---|---|---|
| Polymer | Size | % EE | Size | % EE | Size | % EE |
| hP2-2000H | 208 ± 7 | 49 ± 2 | 211 ± 9 | 49 ± 3 | 206 ± 3 | 50 ± 1 |

While the invention has been particularly shown and described with references to example embodiments thereof, it will be understood by those skilled in the art that various changes in form and details may be made therein without departing from the scope of the invention encompassed by the appended claims.

What is claimed is:

1. A composition comprising:
one or more biodegradable block copolymer drug carriers comprising A-B, A-B-A or B-A-B block copolymers, wherein A is a biodegradable polyester block and B is a polyethylene glycol (PEG) block; and
a plurality of pendent carboxyl groups derived from aromatic or aliphatic dianhydrides incorporated within the backbone of the one or more biodegradable block copolymer drug carriers, wherein at least one pendant carboxyl group of the plurality of carboxyl groups is covalently bonded to a diamine linker.

2. The composition according to claim 1, wherein the diamine linker comprises a first amine that is conjugated to the at least one pendant carboxyl group and a second amine that is covalently connected to a ligand with carboxyl functionality.

3. The composition according to claim 1, wherein at least one pendant carboxyl group of the plurality of carboxyl groups is covalently bonded to a drug, a ligand, a contrast agent, or a near IR-fluorescent agent, directly or via a linker.

4. The composition according to claim 1, wherein at least one pendant carboxyl group of the plurality of carboxyl groups is covalently bonded to a single drug, multiple drugs, or a drug and a ligand.

5. The composition according to claim 3, wherein the drug has at least one of limited aqueous solubility or limited tissue penetration.

6. The composition of claim 1, wherein the composition comprises an aqueous carrier and the composition is a uniform colloidal system.

7. A method of administration comprising:
reconstituting the composition of claim 1 by addition of water or an aqueous solution to form a uniform colloidal system; and
administering the uniform colloidal system to a subject.

8. The method of administration of claim 7, wherein the administering is carried out orally or perorally.

9. The method of administration of claim 7, wherein the administering is by nose, skin, or injection.

10. The composition according to claim 1, wherein the biodegradable polyester block is synthesized from monomers selected from the group consisting of D,L-lactide, D-lactide, L-lactide, D,L-lactic acid, D-lactic acid, L-lactic acid, glycolide, glycolic acid, ε-caprolactone, 1,4-dioxan-2-one, ε-hydroxy hexanoic acid, γ-butyrolactone, γ-hydroxy butyric acid, δ-valerolactone, δ-hydroxy valeric acid, hydroxybutyric acids, malic acid, and a mixture thereof.

11. The composition according to claim 1, wherein the dianhydrides are tetracarboxylic anhydrides.

12. The composition according to claim 11, wherein the tetracarboxylic anhydrides are either pyromellitic dianhydride or cyclohexane tetracarboxylic dianhydride.

* * * * *